(12) United States Patent
Meiri

(10) Patent No.: US 7,488,585 B2
(45) Date of Patent: Feb. 10, 2009

(54) METHOD OF DIAGNOSIS OF PREGNANCY-RELATED COMPLICATIONS

(75) Inventor: Hamutal Meiri, Tel Aviv (IL)

(73) Assignee: Diagnostic Technologies Ltd., Haifa (IL)

( * ) Notice: Subject to any disclaimer, the term of this patent is extended or adjusted under 35 U.S.C. 154(b) by 302 days.

(21) Appl. No.: 10/525,776

(22) PCT Filed: Aug. 28, 2003

(86) PCT No.: PCT/IL03/00706

§ 371 (c)(1),
(2), (4) Date: May 18, 2005

(87) PCT Pub. No.: WO2004/021012

PCT Pub. Date: Mar. 11, 2004

(65) Prior Publication Data

US 2006/0040337 A1     Feb. 23, 2006

(51) Int. Cl.
*C12Q 1/02* (2006.01)
(52) U.S. Cl. ....................................................... 435/29
(58) Field of Classification Search ........................ None
See application file for complete search history.

(56) References Cited

U.S. PATENT DOCUMENTS

| | | | |
|---|---|---|---|
| 4,500,451 A | 2/1985 | Bohn et al. | |
| 5,198,366 A | 3/1993 | Silberman | |
| 5,849,474 A | 12/1998 | Olson et al. | |
| 5,972,594 A | 10/1999 | Heine | |
| 6,548,306 B1 * | 4/2003 | Admon et al. | 436/86 |
| 6,790,625 B1 * | 9/2004 | Paltieli et al. | 435/7.1 |

FOREIGN PATENT DOCUMENTS

| | | |
|---|---|---|
| EP | 0101603 | 2/1984 |
| EP | 0283606 | 9/1988 |
| WO | WO 99/38970 | 8/1999 |
| WO | WO 00/58364 | 10/2000 |
| WO | WO 2004/021012 A3 | 3/2004 |

OTHER PUBLICATIONS

Casanello, P. et al. "Intrauterine Growth Retardation is Associated With Reduced Activity and Expression of the Cationic Amino Acid Transport Systems y+/hCAT-1 and y+/hCAT-2B and Lower Activity of Nitric Oxide Synthase in Human Umbilical Vein Endothelial Cells", Circulation Research, pp. 127-134, 2002.
Malatyalioğlu, E. et al. "Levels of Stable Metabolites of Prostacyclin and Thromboxane $A_2$ and Their Ratio in Normotensive and Preeclamptic Pregnant Women During the Antepartum and Postpartum Periods", *The Journal of Maternal-Fetal Medicine*, vol. 9 pp. 173-177, 2000.
Wang, Y. et al. "Decreased levels of polyunsaturated fatty acids in preeclampsia", *Am. J. Obstet. Gynecol.*, vol. 164(3), pp. 812-818, 1991.
Schiff, E. et al. "Arachidonic Acid Metabolism in the Pathophysiology and Prevention of Preeclampsia- a Review" , *Israel Journal of Medical Sciences*, vol. 27 pp. 578-582, 1991.
Than, N.G. et al. "Isolation and Sequence Analysis of a cDNA Encoding Human Placental Tissue Protein 13 (PP13), a New Lysophospholipase, Homologue of Human Eosinophil Charcot-Leyden Crystal Protein", Placenta, vol. 20 pp. 703-710, 1999.

* cited by examiner

*Primary Examiner*—Cecilia Tsang
*Assistant Examiner*—Amanda P Wood
(74) *Attorney, Agent, or Firm*—The Nath Law Group; Susanne M. Hopkins; Ari G. Zytcer

(57) ABSTRACT

A method for diagnosing pregnancy-related complications in a pregnant woman. The method comprises (a) providing PP13-responding cells having a membrane; (b) exposing the cells to standard PP13; (c) exposing PP13-responding cells to PP13 obtained from the woman, and (d) determining the existence of a modification in the permeability of the cell membrane in (b) and in (c) as a result of exposure to PP13. The modification in permeability in (b) and (c) is then compared, a change in the permeability of (c) as compared to the permeability in (b) indicating the existence of a pregnancy complication in the woman.

22 Claims, 2 Drawing Sheets

METHOD OF DIAGNOSIS OF PREGNANCY-RELATED COMPLICATIONS

FIELD OF THE INVENTION

This invention relates to the use of PP13 in the diagnosis of pregnancy-related complications.

BACKGROUND OF THE INVENTION

The following references are referred to in the text by number:
1. U.S. Pat. No. 4,500,451 to Bohn, et al.
2. WO 99/38970 to Admon et al
3. Than, N. G., et al (1999) Placenta 20:703-710
4. U.S. Pat. No. 5,198,366 to Silberman
5. WO 00/58364 to Paltieli and Rabinovitch
6. U.S. Pat. No. 5,849,474 to Olson, et al.
7. U.S. Pat. No. 5,972,594 to Heine Each year, approximately one of every three pregnant women experiences a pregnancy-related complication, many being related to placental insufficiency. These figures are rising due to, among others, later pregnancies, inadequate nutrition, increased maternal smoking and the higher incidence of multi-fetal pregnancy. Pregnancy-related complications include spontaneous preterm delivery (SPTD), defined as delivery before the 37$^{th}$ gestation week, intrauterine growth retardation (IUGR), associated with the delivery of babies at the lower 3 percentile for age (severe IUGR) or the lower 10 percentile (mild IUGR), and preeclampsia (PE), defined as pregnancy-induced hypertension coupled to proteinuria. These complications negatively impact the outcome of affected pregnancies, at enormous cost both to the patients as well as to health-care systems.

Placental Protein 13 (PP13) is one of the 56 placental proteins identified to date. PP13 was previously isolated from human placental tissue (1, the contents of which are incorporated herein by reference). The protein was characterized by the following parameters: electrophoretic mobility, isoelectric point, sedimentation coefficient, molecular weight determined by ultracentrifugation, molecular weight determined by SDS-PAGE electrophoresis, extinction coefficient and carbohydrate content. The amino acid sequence of PP13 was determined, the full length cDNA was isolated, and the recombinant protein was expressed in various host cells. Sequence analysis revealed resemblence to erthrocyte lysophospholipase A (2). Computer assisted analysis of the deduced amino acid sequence showed that PP13 has the highest homology (56% identity) to the CLC protein, a unique dual-function lysophospholipase. Some authors hypothesize that PP13 is a member of the β-galactosidase binding S-type animal lectin (galectin) superfamily (3). The lysophospholipase activity of PP13 was observed using lysophosphatidylcholine as a substrate.

Utilizing immunoassays based on PP13 and its specific antibody, a test was developed for measuring maternal serum PP13 for predicting pregnancy complication such as severe IUGR, PE and SPTD during pregnancy (4, the contents of which are incorporated herein by reference). Both a radioimmunoassay (RIA) and an enzyme-linked immunosorbent assay (ELISA) were developed using labeled PP13 and anti PP13 polyclonal antiserum, respectively. However, experimental results were given only for the RIA, and not for the ELISA. No further properties of PP13 are disclosed in the Silberman patent. An immunoassay based on the recombinant PP13 is described in WO 99/38970. Subsequently, a more advanced method based on monoclonal antibodies to PP13 and recombinant PP13 was disclosed (5).

There have also been reports in the literature regarding the determination of other placental proteins and their relationship to pregnancy disorders.

A method of diagnosing preeclampsia in a pregnant female by detecting significantly elevated levels of a hemoglobin variant or its precursor, or a red blood cell glycolytic enzyme or its precursor has been disclosed (6).

A method of screening reproductive tract disease, inflammation and preeclampsia in humans by measuring the level of human neutrophil peptide defensins in a sample of bodily fluids has also been disclosed (7). Other measured parameters are beta HCG, PAPP-A, fetal fibronectin or estriol.

SUMMARY OF THE INVENTION

It is an object of the present invention to provide a method for diagnosing pregnancy-related complications in a pregnant woman.

It is a further object of the present invention to provide a diagnostic kit for use in the method of the invention.

In a first aspect of the invention, there is provided method for diagnosing pregnancy-related complications in a pregnant woman comprising:
(a) providing PP13-responding cells having a membrane;
(b) exposing said cells to standard PP13;
(c) exposing PP13-responding cells to PP13 obtained from said woman, the cells of step (c) being:
  i) other than the cells of step (b) or
  ii) the same as the cells of step (b), but after sufficient washing to remove the standard PP13;
(d) determining the existence of a modification in the permeability of the cell membrane in (b) and in (c) as a result of exposure to PP13; and
(e) comparing the modification in permeability in (b) and (c), a change in the permeability of (c) as compared to the permeability in (b) indicating the existence of a pregnancy complication in said woman.

It has now been discovered that not only can PP13 be used as a marker to detect pregnancy-related disorders in general, but also that PP13 derived from affected pregnant women can assist in better identifying the underlying changes in the normal course of placental differentiation that led to the development of the pregnancy complications. A comparison of the effects of PP13 derived from a pregnant women at risk to develop these complication to the effects of PP13 standards isolated from unaffected or normal pregnant women can be utilized to identify the biochemical and physiological processes that are impaired in the relevant pregnancy pathologies, thereby providing an indication of the identity of the disorder. In other words, a differential diagnosis of a number of pregnancy pathologies may be obtained by measuring various aspects of the multi-facet response to PP13. This can enable diagnosis at an early stage, prior to the development of clinical manifestations of the disorders. In this way, potential new methods of clinical manifestations may be applied to prevent the development of clinical symptoms, or at least decrease their severity.

In its first aspect, the method of the invention is based on the ability of PP13 to modify the permeability of PP13-responding membranes, and particularly placental trophoblast membranes, to ion flow. Without restricting the invention in any way, it is believed that PP13 increases the permeability of placental trophoblast membranes to cations, and particularly to calcium ions, and that PP13 obtained from pregnant women suffering from certain pregnancy-related complications has an impaired effect on these permeability changes. It has been found that PP13 obtained from pregnant women suffering from IUGR, and particularly severe (type II) IUGR, has a decreased effect on trophoblast membrane permeability compared to PP13 standards obtained from healthy pregnant women.

PP13 standards may be obtained either by expression from recombinant DNA encoding PP13 in host cells (bacteria, mammalian, etc), by PCR amplification with oligonucleotide primers of the recombinant DNA encoding PP13 and its in-vitro translation into protein, or by purification of PP13, e.g. from human placenta or from trophoblast cell lines. In all cases, PP13 standards obtained from normal human placenta or other normal human tissues or both fluids can be confirmed to have the amino acid sequence as previously described (2).

In the context of the present specification, a normal human placenta is defined as a placenta of a healthy woman who delivered in term a healthy baby (=normal pregnant woman).

In the present invention, the term "determining" includes both qualitative as well as quantitative determinations. The term "significant" as in a "significant difference" between standards and samples, is defined, in cases of a qualitative comparison, as a difference of 50% or more between the measured values of the standard and the sample, all other parameters remaining the same. For a quantitative comparison, it is defined as a statistical difference between standards and samples with P<0.001 for the comparison of the differences.

In a preferred embodiment, standard PP13 is verified by the following criteria:
(1) MW of approximately 16 Kda in SDS PAGE under reducing conditions;
(2) the full length DNA sequence and its deduced or measured amino acid sequence as disclosed in WO 99/38970; and
(3) recognized by the MAbs 27-2-3 and/or 215-28-3 as disclosed in WO 00/58364 (hybridoma deposited in accordance with the Budapest Treaty at the Collection Nationale de Cultures de Microorganismes of the Pasteur Institute of 25, Rue du Docteur Roux, Paris, France, and accorded Accession Nos. I-2135 and I-2136, respectively).

PP13 may be obtained from a pregnant woman in a number of ways.

Non-Limiting Examples Include:
(a) a purified preparation from body fluids, particularly amniotic fluid;
(b) PP13-encoding DNA isolated from human placenta and expressed in host cells or in a cell-free preparation;
(c) after purification from the placenta or other tissue sources, or from maternal placenta derived primary cultures or immortalized cell lines;
(d) by chorionic vilouse sampling (CVS) or their derived placenta tissue cultures or cultured trophoblasts; and
(e) from miscarriage or abortion tissues.

Examples of PP13-responding cells include primary cultured trophoblasts, immortalized trophoblast cell lines and placental organ culture.

The method of the invention in this aspect may be carried out in a number of preferred embodiments.

In one embodiment, the effect of PP13 on depolarization of PP13-responding cells having a membrane is measured. Changes in membrane potential of trophoblast cells may be measured by a number of known, conventional methods. Defining PP13 as an analyte, this embodiment may be carried out, for example, by measuring the changes in membrane potential produced by exposure to the analyte using a cell membrane electrode. Examples of such electrodes include: (a) a patch-clamp microelectrode filled with an electrolyte solution resembling the intracellular fluid and measuring the voltage difference produced between the inside of the electrode and the extracellular fluid in response to the analyte; and (b) intracellular microelectrodes filled with an electrolyte that measure the voltage differences between the cell interior to its exterior in response to the analyte. An alternate possibility is to measure the fluorescence light emitted by voltage sensitive dyes embedded in the trophoblast cell membrane thereby following changes in trophoblast cell membrane potential (Grinvald A., R. Hildesheim, I. C. Farber and L. Anglister. *Better fluorescent probes for the measurements of rapid changes in membrane potential*. Biophys. J. 39, 301-308 (1982); Grinvald A., A. Fine, I. C. Farber and R. Hildesheim. *Fluorescence monitoring of electrical responses from small neurons and their processes*. Biophys. J. 42, 145-198 (1983)).

In each of these cases it is possible to compare the response elicited by a known amount of a PP13 standard to the response elicited by PP13 obtained from a pregnant woman. The results may be qualitative, i.e. normal or abnormal, or may be quantitative. In the later case, a dose response curve may be prepared using a set of PP13 standards, made of a series of increasing amount of standard PP13 concentrations, and plotting the peak of the membrane depolarization change elicited by PP13 vs. PP13 concentration. Subsequently, a known amount of PP13 from a pregnant woman subject is added, and the response is measured and plotted on the same dose response curve to obtain the relative potency of the PP13 samples from the pregnant woman. The parameters used for comparison may be the mean difference in the amplitude of the depolarization or the derivative of membrane depolarization vs. time (dV/dt) or the sensitivity (defined as the ratio of the amplitude of depolarization change using the subject PP13 (c) vs. the depolarization change of the standard PP13 (b), or $D_{(c)}/D_{(b)}$). A significant difference (i.e. a difference larger than 1.5 units of the standard error of the means (SEM) on both sides) would indicate the existence of an impaired response (increased or decreased) to PP13 associated with pregnancy complications in the subject.

To verify if the depolarization is dependent on membrane permeability to calcium ions, the method of the invention may be carried out in the presence of calcium chelators or blockers. If the response to PP13 is thereby blocked or prevented, it implies that the depolarization is calcium ion dependent.

In a second embodiment, the effect of PP13 on PP13-responding cells having a membrane is measured by the effect of PP13 on inward ion current. This may be carried out by a number of known, conventional methods. Non-limiting examples include measuring the ion current with cell membrane electrode(s) as described above in the first preferred embodiment, or measuring the current using membrane embedded current-sensitive dyes.

In a preferred embodiment, the identification of the inward current as a current carried by calcium ions is performed as described above for the calcium dependent depolarization. For example, the testing can be performed using calcium ion chelators or calcium channel blockers which block or prevent the calcium current, thereby acting as controls to ensure the calcium specificity of the inward current. The results may be qualitative, i.e. normal or abnormal, or may be quantitative. In the later case, a dose response curve may be prepared using PP13 standards. Subsequently, samples of known amounts of PP13 from the pregnant woman are applied to the PP13-responding cells and the effects of various concentration of PP13 are measured and plotted on the dose response curve to verify their relative potency as compared to PP13 standards.

The modification of inward ion current may be measured in terms of the amplitude of the current change and/or the slope of the current change (dI/dt, where dI is the derivative of the current changes vs. time), or in terms of the sensitivity of the current change (defined as the ratio of the amplitude of the current change elicited using the subject PP13 (c) vs. the amplitude of the current change in response to PP13 standard (b) or $I_{(c)}/I_{(b)}$).

In a third embodiment, the direct calcium dependent effect of PP13 on PP13-responding cells having a membrane is measured by specific calcium sensitive electrodes or calcium sensitive dyes. The measurements may be carried out by a number of known, conventional methods. Non-limiting examples include measuring the calcium current with a calcium-ion specific cell membrane electrode, or by calcium sensitive dyes. In the latter case, one is measuring the fluorescence emitted by membrane embedded calcium-sensitive dyes (Anglister L., I. C. Farber, A. Shahar and A. Grinvald. *Localization of voltage-sensitive Ca++ channels along developing neurites; their possible role in regulating neurite growth*. Dev. Biol. 94, 351-365 (1982)) or measuring the calcium influx using radiolabeled calcium ions.

In a preferred embodiment, the calcium specificity I is further verified with calcium chelators or blockers to block or diminish the current, radioactive ion flux or fluorescence produced in response to the analyte, and thus ensure assay specificity. The results may be qualitative, i.e. normal or abnormal, or may be quantitative. In the latter case, a dose response curve may be prepared using PP13 standards, and the maximal transient calcium current elicited by various PP13 standard concentrations may be plotted vs. the log concentration of PP13. The relative potency of the PP13 sample from a pregnant woman may be determined by plotting the calcium current elicited by her PP13 on the curve.

In a further embodiment, there is provided a kit for diagnosing pregnancy complications in a pregnant woman comprising:
  (a) PP13 standards; and
  (b) a voltage sensitive dye.

In a still further embodiment, there is provided a kit for diagnosing pregnancy complications in a pregnant woman comprising:
  (a) PP13 standards; and
  (b) a calcium sensitive dye.

In another embodiment, there is provided a kit for diagnosing pregnancy complications in a pregnant woman comprising:
  (a) PP13 standards; and
  (b) a current sensitive dye.

In a preferred embodiment, the kits may include one or more of the following additional components:
  1. one or more physiological solutions such as (1) external physiological medium, (2) electrode internal electrolyte solution, and (3) assay buffer for dissolving PP13 for physiological recording to measure membrane potential and ion currents combined with pH measurement paper;
  2. a calcium chelator and/or calcium blocker standard solution to verify calcium sensitivity of the parameters measured by the method of the invention;
  3. a testing chamber for performing the testing; and
  4. a set of electrodes for measurements.

In a second aspect of the invention, there is provided a method for diagnosing pregnancy-related complications in a pregnant woman comprising:

(a) providing a membrane phospholipid suspension;
  (b) exposing a first portion of said suspension to standard PP13;
  (c) exposing a second portion of said suspension to PP13 obtained from said woman;
  (d) determining the level of hydrolysis of the phospholipids to free fatty acids in (b) and (c); and
  (e) comparing the level of hydrolysis in (b) and (c), a change in the level of hydrolysis of (c) as compared to the level of hydrolysis in (b) indicating the existence of a pregnancy-related complication in said woman.

In this second aspect, the method of the invention is based on the ability of PP13 to cause the release of free fatty acids from a phospholipid suspension. Non-limiting examples of such fatty acids include arachidonic acid (AA), linoleic acid (LA), or other members of the saturated or un-saturated fatty acid family, which are components in the structure of membrane phospholipids. The phospholipid suspension may be, for example, (a) isolated or whole cell or tissue culture membranes; (b) a cell-free biological phospholipid suspension; or (c) a cell-free artificial phospholipids suspension, both in a monolayer, bilayer or liposome format. A change in the amount, composition or LA/AA ratio of fatty acids which are released from the phospholipid suspension in response to PP13 obtained from a subject may indicate that the subject is suffering from IUGR, preeclampsia or both.

In a preferred embodiment, the amounts ($S_{max}$) and composition of free fatty acids released from a membrane phospholipid suspension in response to a set of concentration growing standards (or a reference concentration of standard) (b) and a known concentration sample (c) PP13 are measured and determined. The derivative of free fatty acid release vs time ($dS_{max}/dt$) is determined for each, and the sensitivity of the concentration of free fatty acid released ($S_{max}$)(c) vs. ($S_{max}$)(b), for a given embodiment concentration, or of the kinetics of their release ($dS_{max}/dt$)(c) vs. ($dS_{max}/dt$) (b) is calculated. A significant difference between (b) and (c) indicates the existence of a pregnancy-related complication in the examined subject.

In a further embodiment, there is provided a kit for diagnosing pregnancy-related complications in a pregnant woman comprising:
  (a) PP13 standards; and
  (b) fatty acid standards; and, optionally,
  (c) developing regents to detect free fatty acids and their derivatives.

In a preferred embodiment of the kit, the fatty acid standards are selected from the group consisting of LA and AA.

In a still further preferred embodiment, the kit may further comprise one or more of the following:
  (a) a phospholipid suspension;
  (b) one or more assay buffers to prepare the phospholipid suspension, expose it to the PP13 standards, wash out the PP13 and measure the amount of free fatty acids using the fatty acid standards;
  (c) a chamber to perform the test; and
  (d) TLC plates for phospholipid chemical verification or NMR standards for phospholipid spectrum verification.

In a further aspect, the method of the invention is based on a combination of the first two aspects of the invention. This combination provides means to perform a comprehensive differential diagnosis of pregnancy-related complications in a pregnant woman in order to better understand the anticipated complication.

For example, by measuring cell membrane depolarization, inward current, calcium influx, and LA and AA amounts produced in the presence of PP13 obtained from a pregnant woman as compared to standard PP13, the following diagnoses may be made:
(a) a low amount of linoleic acid while all other tests are normal indicates a condition of mild (type I) IUGR;
(b) a low amount of linoleic acid and arachidonic acid, low depolarization and calcium current and normal inward current indicates a condition of severe (type II) IUGR;
(c) a low amount of linoleic acid and a high amount of arachidonic acid, while all other tests are normal indicates a condition of mild (type I) preeclampsia;
(d) a low amount of arachidonic acid, while all other tests are normal indicates a condition of severe (type II) preeclampsia;
(e) all tests give low results indicates a condition of combined IUGR and preeclampsia; and
(f) all tests are normal indicates the pregnancy is normal.

In a third aspect of the invention, there is provided a method for diagnosing pregnancy-related complications in a pregnant woman comprising:
(a) providing a membrane phospholipid suspension;
(b) exposing a first portion of said suspension to standard PP13;
(c) exposing a second portion of said suspension to PP13 obtained from said woman;
(d) measuring the production of prostaglandins in (b) and (c); and
comparing the amounts of prostaglandins produced in (b) and (c), a change in the amount of prostaglandins of (c) as compared to the amount of prostaglandins in (b) indicating the existence of a pregnancy-related complication in said woman.

In this aspect of the invention, exposure to PP13 is followed by the production of prostaglandins. In a preferred embodiment, the prostaglandins are prostacyclin (PCN) and/or thrombaxane (THX) or their metabolites.

A differential diagnosis of pregnancy-related complications in a pregnant subject may be obtained by measuring the amounts of different prostaglandins produced in the presence of PP13 obtained from a subject as compared to normal PP13. For example:
(a) the production of a low amount of PCN and a normal amount of THX in response to PP13 indicates a condition of mild (type I) IUGR;
(b) a low amount of PCN and a low amount of THX indicates a condition of severe (type II) IUGR;
(c) a low amount of PCN and a high amount of THX indicates a condition of mild (type I) preeclampsia;
(d) a normal amount of PCN and a high amount of THX indicates a condition of severe (type II) preeclampsia;
(e) low amounts of both PCN and THX indicate a condition of combined IUGR and preeclampsia; and
(f) normal amounts of PCN and THX indicate the pregnancy is normal.

In a still further aspect of the invention, there is provided a measuring apparatus for use in diagnosing pregnancy-related complications in a pregnant woman, the apparatus comprising:
(a) a measuring unit operable to measure modifications in the permeability of the membrane of PP13-responding cells and generate measured data indicative thereof; and
(b) a control unit having:
i) a memory utility for storing reference data indicative of normal modification in the permeability of the membrane of a PP13-responding cell as a result of exposure to standard PP13; and
ii) a data processing utility pre-programmed to be responsive to measured data obtained by using PP-13 obtained from a pregnant woman, for processing said measured data by comparing it with the reference data, and generating output data indicative of a difference between them, thereby enabling diagnosis of pregnancy-related complications.

The above described technique may be implemented by a suitable measuring unit and control unit connectable thereto (wired or wireless) specifically pre-programmed for processing the measured data. The measuring unit may be any known type for applying electrical or optical measurements to a PP-13 responsive cell. The measurements are aimed at detecting an effect of PP-13 on the membrane permeability of the cell, e.g. depolarization, ion current, etc.

The control unit is typically a computer system, which may or may not be an expert system, and comprises such main functional elements as a memory utility, a data processing utility and a user interface utility. The processing utility is pre-programmed to be responsive to the measured data obtained by using PP-13 obtained from a pregnant woman for processing said measured data by comparing it with certain reference data, and generating output data indicative of a difference between them, if such exists. The reference data is that indicative of normal modification in the permeability of the membrane of a PP13-responding cell as a result of exposure to standard PP13. This reference data can be obtained concurrently while measuring the effect of PP13 taken from a pregnant woman or may be previously measured and stored in the memory utility. The results of processing thus enable diagnosing pregnancy-related complications, in the event that a difference exists.

DESCRIPTION OF THE DRAWINGS

In order to understand the invention and to see how it may be carried out in practice, a preferred embodiment will now be described, by way of non-limiting example only, with reference to the accompanying drawings, in which:

FIG. 1 shows a comparison of the effect on depolarization of placental membranes of normal PP13 (FIG. 1A) to the effect of PP13 obtained from a pregnant woman suffering from IUGR (FIG. 1B).

The depolarization was measured in two ways:
(i) The smooth line shows the transient cell membrane depolarization (mV scale on the left Y-Axis) as measured by a cell patch-clamp electrode filled with electrolyte solution similar to the intracellular medium. The electrolyte solution was comprised of 100 mM KCl, 10 mM NaCl, 0.6 mM MgCl2, 10 mM Tris-HCl adjusted to pH=7.4 and 50 mM Manitol, as compared to the extracellular solution of 150 mM NaCl, 3 mM KCl, 2 mM MgCl2, 10 mM Tris-HCL pH=7.4. The membrane potential was recorded by Axo-Patch, 200b, a patch clamp amplifier of Axon Instruments Inc. Union City, Calif., USA.
(ii) The broken line shows the fluorescence light emitted by a voltage sensitive dye of the dialkylaminophenylpolyenylpyridinium dye group (in this case RH 414, but RH 795 or RH-237 or RH 421 (all of Molecular Probes, Eugene, Oreg., USA). The dye was used at 0.1 mg/ml (but effective concentration range can vary between 0.05-0.2 mg/ml) and was incubated for 30 minutes prior to the application of PP13 to ensure dye embedding in the trophoblast membrane. In response to PP13, the depolarization causes fluorescence light emission (OD on the right Y Axis) which is detected by a photodiode multiplexure Neuroplex System, Photodiode Array System (Red Short LLP, New Haven, Conn., USA) Nemodel WuTech H-469IV photodiode array system: 1.6 KHz (full frame), 24×24 pixels, very large dyanmic range (>17 bits) placed above the culture and a CCD Camera Model NeuroCCD-SM, low dark noise cold CCD imaging system (SAS SciMeasure Analytical Systems, Inc.,) of 80×80 pixels, Full-frame, frame rate: 2,000 Hz, 3×3-binning, frame rate: 5,000 Hz, Back-illuminated for high quantum efficiency (80% from 400-600 nm), Cooled CCD: for low dark noise, Read Noise of 2,000 Hz: 26 e-, 1,000 Hz: 9 e-, 125 Hz: 4 e-, 40 Hz: 3 e-. Large well size: 300,000 e-, Digitization: 14 binds standard; 16-bits optional (slower frame rate), No fan, Frame transfer to minimize smear; transfer time 7 micro-seconds, The SciMeasure camera uses the outstanding Marconi CCD39-01 CCD ch.

Figure 1A:
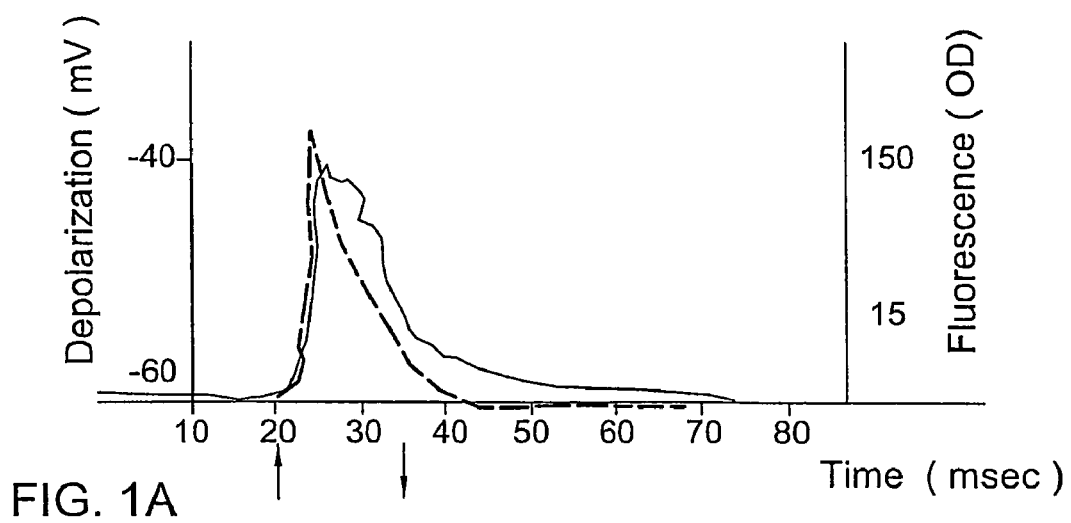
In FIG. 1A, PP13 was obtained from the placenta of a woman who delivered in time (gestation week 39) a normal baby and 30 pg/mL of PP13 was applied for 15 mseconds (up-ward and downward arrows on the X-axis) to cultured trophoblast cells obtained from $26^{th}$ gestation week placenta. Cells were cultured for 48 hours and measurements were made from single nucleated cells.
Figure 1B:
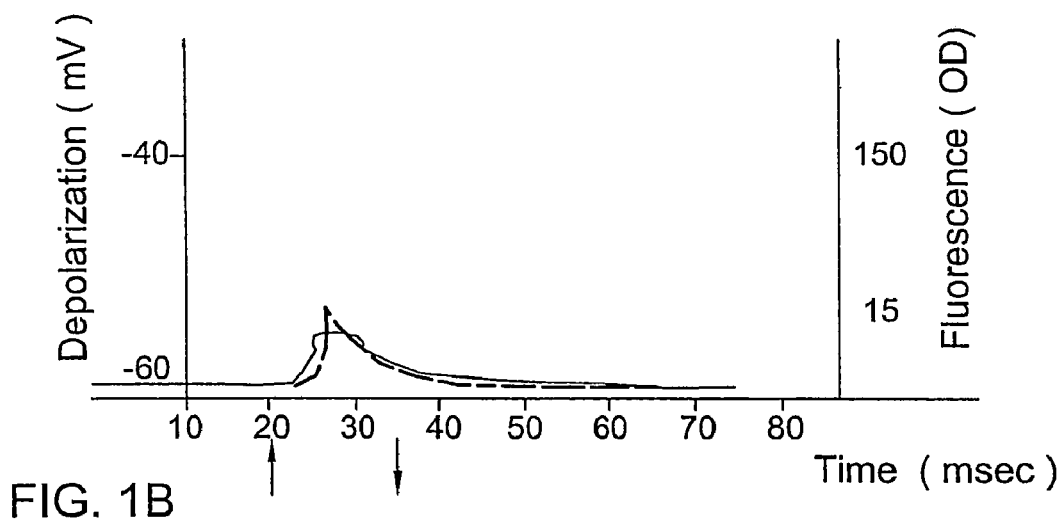
In FIG. 1B the PP13 was taken from severe IUGR (the woman delivered at the $39^{th}$ gestation week a baby at the lower 3% weight for the gestation week).
Figure 2:
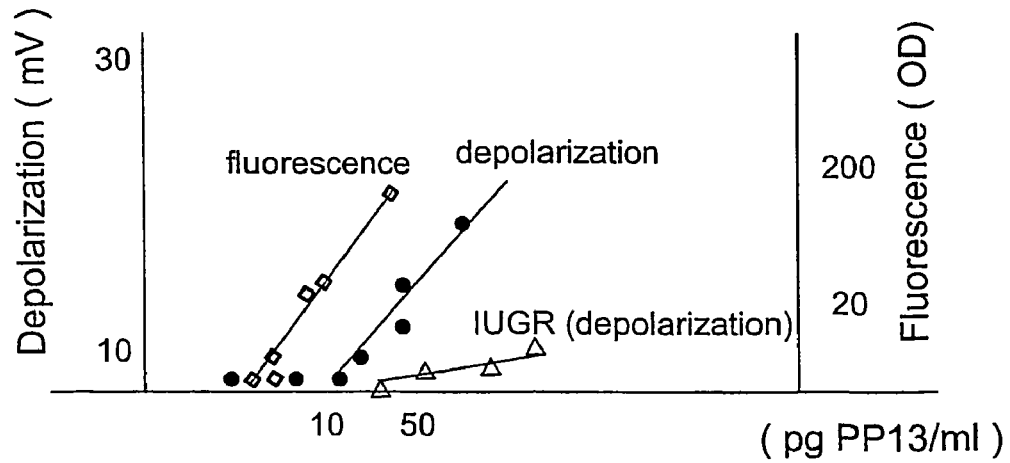

FIG. 2 shows a plot of the peak transient depolarization (mV) (●) or the amplitude of the fluorescence emission transient in optical density (OD) (□) vs. the Log of the concentration of the PP13 applied in the range of 10 to 100 pg PP13/ml. The trophoblasts were exposed each time to a given standard $PP_{13}$ concentration taken from normal pregnancy, followed by 15 minutes wash-out prior to the subsequent exposure to the next $PP_{13}$ concentration. The depolarization was also measured using PP13 from the IUGR case of FIG. 1 (Δ).

Figure 3A:
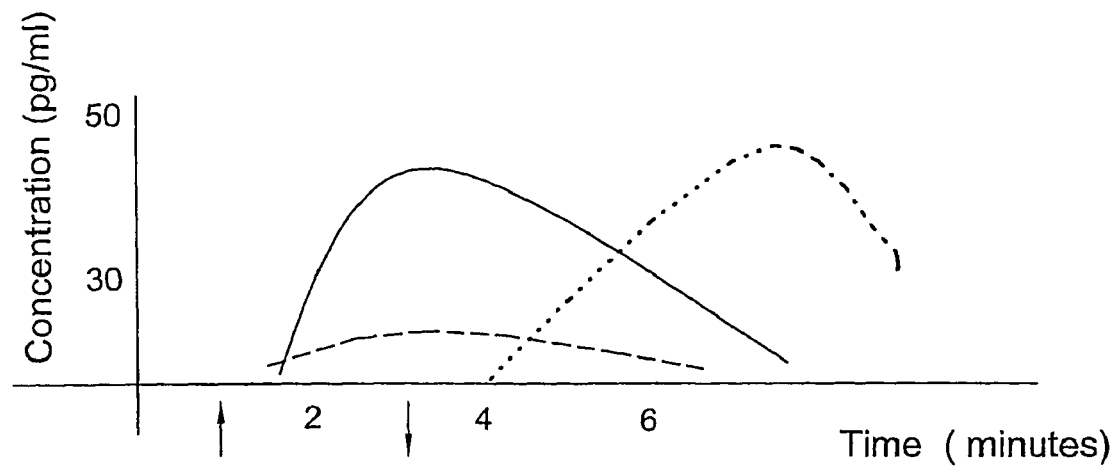
Figure 3B:
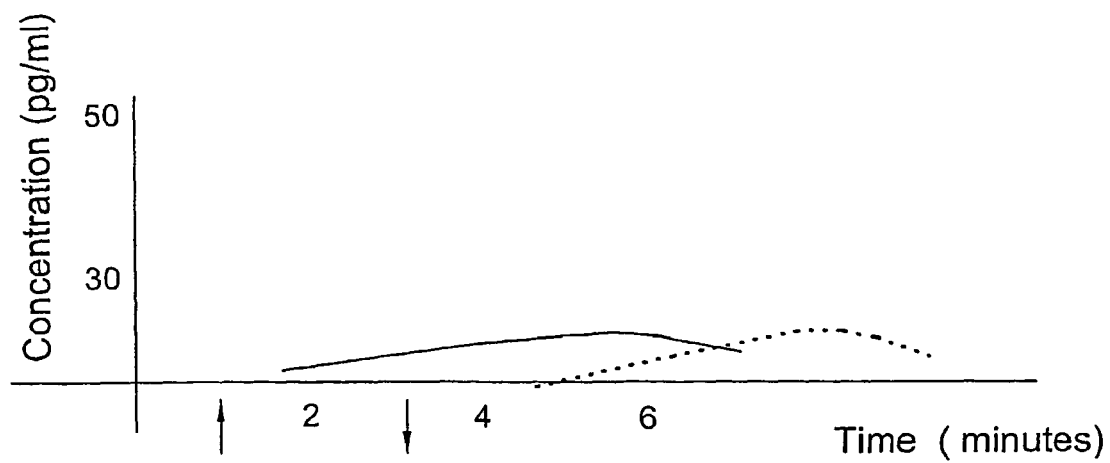

FIG. 3 shows the PP13-dependent transient release of linoleic acid from trophoblasts cultured for 48 hours and then exposed to a 2 minute wash-in/wash-out (upward/downward arrows on the X-axis) of 30 pg/ml PP13. The Y axis indicates concentration of the various measured compounds: linoleic acid (solid line); prostacyclin (dotted line) and linoleic acid released in the presence of 10 mM ethyleneglycoltetracetic acid (EGTA) (broken line). FIG. 3A: PP13 standards from the placenta of women who delivered in time a normal baby at gestation week 39; FIG. 3B: PP13 isolated from the placenta of women who delivered in gestation week 36 following severe preeclampsia.

DETAILED DESCRIPTION OF SPECIFIC EMBODIMENTS

EXAMPLE I

Trophoblast cells were cultured from $26^{th}$ gestation week placenta following cell isolation by a combined colagenase and DNAase treatment followed by a Ficoll gradient as described by Yagel, S., Parhar. R. S. Jeffrey, J. J. and Lala, P. K (1988) *Normal nonmetastatic human trophoblast cells shae in vitro invasive properties of malignant cells*. J. Cell physiol. 136: 455-462. The cells were plated on a glass cover slide coated with an extracellular matrix of human endometrium cells placed in tissue culture dishes and supplemented with RPMI culture medium, antibiotics and 3% calf serum. The cells were cultured for 48 hours.

Before use, the cover slide was placed in the physiological recording chamber containing a reference electrode and placed under a photomultiplexor diode connected to a recorder. The culture was perfused first with the physiological solution composed of 150 mm NaCl, 3.1 mM KCl, 0.6 mM MgCl2 and 10 mM Tris-HCl, pH=7.4, and then exposed for 30 minutes to the above physiological solution containing dialkylaminophenylpolyenylpyridinium dye group (in this case RH 414, but RH 795 or RH-237 or RH 421 (all of Molecular Probes, Eugene, Oreg., USA) are also suitable. The dye was used at 0.1 mg/ml (but effective concentration range can vary between 0.05-0.2 mg/ml) and was incubated for 30 minutes prior to the application of PP13 to ensure dye embedding in the trophoblast membrane. The excess dye is then washed out. Recording from single trophoblasts is performed by way of a glass patch-clamp electrode filled with 120 mM KCl, 10 mM NaCl, 50 mM Manitol, 10 mM Tris-HCl, pH=7.4. The culture is then exposed for 15 msec (between up-ward and downward arrows on the X-axis) to a PP13 standard at 30 pg/ml (FIG. 1A) followed by a prolonged (30 min) wash-out. The same cell culture was subsequently exposed to 30 pg/ml of PP13 obtained from a women who developed IUGR (IUGR PP13) (FIG. 1B). Measurements of either cell membrane depolarization or photo-emission were made from single nucleated cells.

As can be seen in FIGS. 1A and 1B, a depolarization from −60 mV to −35 mV was measured by the cell membrane electrode using 30 pg/ml of PP13 standard, while the depolarization with 30 pg/ml of IUGR PP13 was negligible. The same cell showed an emission of 1500 nano-OD units using normal PP13, while the light emission with IUGR PP13 was also negligible. The transient light emission was similar in time and shape to the depolarization change in the cell membrane. The transient response disappeared when PP13 was washed-out from the medium.

This shows that a PP13-induced depolarization can be utilized as a test to diagnose IUGR.

EXAMPLE II

The experiment was carried out as described in Example I, but the trophoblast cells were exposed each time to a given PP13 concentration for 15 msec, followed by a washout for 15 minutes prior to the subsequent exposure to the next PP13 concentration. The results are shown in FIG. 2.

It can be seen that with standard PP13, a linear slope of depolarization vs. PP13 can be plotted in both methods of depolarization measurements. In both cases the slope obtained is 29 as anticipated from the Nernest equation of $V_m=[-58/(^e)] \times \log$ of $[C^e]_{out}/[C^e]_{in}$ where $^e$ is the cation charge, [C] is the concentration of a respective cation and the out and in refer to the outside and inside concentration of the respective cation. When e=2 (as in the case of calcium), and assuming no change in the external (2 mM) and internal (1 μM) calcium concentration, the depolarization is supposed to have a slope of 29 if produced by calcium ions. For PP13 taken from a pregnant woman suffering from IUGR, there is only a negligible depolarization which is not only shifted to the right, but also of a much lower slope indicating a significant difference in the response to PP13 standard vs. IUGR-PP13. This shows that a PP13-induced depolarization can be utilized as a quantitative test to diagnose IUGR.

EXAMPLE III

Trophoblasts were cultured for 48 hours as described above and then exposed to 30 pg/ml PP13 taken either from a woman with normal pregnancy (FIG. 3A) or from a pregnant woman suffering from preeclampsia (FIG. 3B).

As can be seen in FIG. 3A, a transient elevation of linoleic acid (LA) of at least 50 pg/ml (Y Axis) from the trophoblast membrane followed its release from the phospholipid constituent of the cell membrane in response to the short exposure of the trophoblasts to PP13's enzymatic activity. The transient elevation of LA continues longer than the exposure to PP13 (X-Axis) and is subsequently degraded as the LA turned into prostacyclin, for which it is served as a precursor. LA is a component of membrane phospholipids and is released from the complete molecule due to its hydrolysis mediated by a short exposure to the PP13 enzymatic activity as a lysophospholipase A.

If the process is repeated after pre-incubating the trophoblasts with a medium containing 10 mM EGTA (a calcium ion chelator), and the response to PP13 is superimposed on the same time basis and scale, the release of LA is significantly diminished to a maximum of 15 pg/ml. This indicates the calcium dependency of the process, as was also indicated above by the transient depolarization carried by the divalent cation in FIGS. 1 and 2.

When the PP13 is taken from a woman suffering from preeclampsia there is only a negligible prostacyclin response. This shows that a PP13-induced linoleic acid release test or a prostacyclin production test can either together or individually be utilized as tests to diagnose preeclampsia.

EXAMPLE IV

The establishment of the normal response to PP13 is performed with PP13 standards obtained from 10 different normal pregnant women. The normal PP13 preparation was each tested on 5-7 different preparations of cultured trophoblasts 2 phospholipid preparations and in 2 liposome studies.

In each normal and affected woman, the level of PP13 in the maternal serum was detected in gestation weeks 16-20 and 24-28 by sandwich ELISA. The calibration of PP13 concentration was also determined by sandwich ELISA using PP13 standards. PP13 primary sequence was verified following protein sequencing or after PCR and DNA sequence.

IUGR-PP13 and preeclampsia PP13 were obtained by two different methods—(a) purification from maternal placenta; and (b) preparation of genomic library of the placenta, designing of constructs from the cDNA, isolation of the PP13 clones, insertion into *E-Coli*, expression in *E-Coli* and purification of PP13 standards verified by sequence analysis, SDS-PAGE, immunoblotting and protein determination.

The PP13 of pregnancy complication was obtained from:
(a) 3 cases of mild IUGR (baby born at the 5% lower percentile per gestation age);
(b) 2 cases of severe IUGR (baby born at the 3% lower percentile per gestation age);
(c) 3 cases of mild preeclampsia (gestational hypertension of >90/140 and proteinuria about +2 in deep stick developed at gestation week 37);
(d) 2 cases of severe preeclampsia (gestational hypertension of >90/140 and proteinuria above +2 in deep stick developed at gestation week 30); and
(e) 1 case of severe preeclampsia+severe IUGR.

TABLE 1

Differential Diagnosis summerizing the results of 6 different tests.
(Each test can be Normal (N), Lower than Normal (L) or higher than Normal (H))

| Subject Test | Normal | (a) | (b) | (c) | (d) | (e) |
|---|---|---|---|---|---|---|
| Inward current | N | N | N | N | N | L |
| Ca Current | N | N | L | N | N | L |
| Depolarization | N | N | L | N | N | L |
| Arachidonic Acid | N | N | L | H | L | L |
| Linoleic Acid | N | L | L | L | N | L |
| Psotacyclin | N | L | L | L | N | L |
| Trombaxane | N | N | L | H | H | L |
| Serum PP13 level by Sandwich ELISA GW 16-20 and 24-28. | N | L | L | L | L | L |
| Diagnosis | Normal pregnancy | IUGR Type 1 associated with Abnormal Oxygenation | IUGR type II Impaired implantation | Preeclampsia Type 1 | Preeclampsia Type II High Blood Pressure | Preclampsia + IUGR associated with High Blood Presure and restricted fetal growth |

The invention claimed is:

1. The method for diagnosing pregnancy-related complications in a pregnant woman comprising:
   (a) providing PP13-responding cells having a membrane;
   (b) exposing said cells to standard PP13;
   (c) exposing PP13-responding cells to PP13 obtained from said woman, the cells of step (c) being:
      i) other than the cells of step (b) or
      ii) the same as the cells of step (b), but after sufficient washing to remove the standard PP13;
   (d) determining the presence of a modification in the permeability of the cell membrane in (b) and in (c) as a result of exposure to PP13; and
   (e) comparing the modification in permeability in (b) and (c), a change in the permeability of (c) as compared to the permeability in (b) indicating the presence of a pregnancy complication in said woman.

2. The method according to claim 1 wherein the modification in membrane permeability is determined by measuring cell membrane depolarization.

3. The method according to claim 2 wherein the cell membrane depolarization is measured using a cell membrane electrode or a voltage-sensitive dye.

4. The method according to claim 1 wherein the modification in membrane permeability is determined by measuring inward ion current.

5. The method according to claim 4 wherein the inward ion current is measured using a cell membrane electrode or a current-sensitive dye.

6. The method according to claim 1 wherein the modification in membrane permeability is determined by measuring calcium influx.

7. The method according to claim 6 wherein the calcium influx is measured using a cell membrane electrode, a calcium-sensitive dye or radio-labeled calcium ions.

8. The method according to claim 1 wherein said pregnancy-related complication is intrauterine growth retardation (IUGR).

9. The method according to claim 1 wherein said PP13-responding cells are selected from the group consisting of primary cultured trophoblasts, immortalized trophoblast cell lines and placental organ culture.

10. The method according to claim 1 wherein said PP13 obtained from said woman is in a form selected from the group consisting of:
  a. a purified preparation from body fluids;
  b. PP13-encoding DNA isolated from the woman and expressed in host cells or in a cell-free preparation; and
  c. after purification from the placenta.

11. The method according to claim 10 wherein purification from the placenta is selected from the group of maternal placenta derived primary cultures, chorionic villus sampling (CVS) or their derived placenta tissue cultures or cultured trophoblasts and miscarriage or abortion tissues.

12. The method according to claim 1 wherein the membrane permeability is measured quantitatively with reference to a dose response curve prepared using PP13 standards.

13. A kit for diagnosing pregnancy complications in a pregnant woman comprising:
  a. PP13 standards; and
  b. a dye selected from a voltage sensitive dye, a calcium sensitive dye and a current sensitive dye.

14. A kit according to claim 13 further comprising a calcium chelator and/or calcium blocker preparation.

15. A method for diagnosing pregnancy-related complications in a pregnant woman comprising:
  a. providing a membrane phospholipid suspension;
  b. exposing a first portion of said suspension to standard PP13;
  c. exposing a second portion of said suspension to PP13 obtained from said woman;
  d. determining the level of hydrolysis of the phospholipids to free fatty acids in (b) and (c); and
  e. comparing the level of hydrolysis in (b) and (c), a change in the level of hydrolysis of (c) as compared to the level of hydrolysis in (b) indicating the existence of a pregnancy-related complication in said woman.

16. The method according to claim 15 wherein said membrane phospholipid suspension is selected from the group consisting of:
  a. isolated or cell culture membranes;
  b. a cell-free biological phospholipid preparation; and
  c. a cell-free artificial phospholipid preparation.

17. The method according to claim 15 wherein the level of hydrolysis is determined by determining the release of free fatty acids.

18. The method according to claim 15 wherein said fatty acids are arachidonic acids (AA) and/or linoleic acids (LA).

19. The method according to claim 15 wherein said pregnancy-related complication is IUGR and/or preeclampsia.

20. A kit for diagnosing pregnancy-related complications in a pregnant woman comprising:
  a. PP13 standards;
  b. fatty acid standards; and, optionally,
  c. developing reagents to detect free fatty acids and/or their derivatives.

21. A kit according to claim 20 wherein said fatty acid standards are selected from the group consisting of LA and AA.

22. A method for the differential diagnosis of pregnancy-related complications in a pregnant woman comprising tests which measure cell membrane depolarization, inward current, calcium influx, and LA and AA amounts, and wherein:
  a. a low amount of linoleic acid while all other tests are normal indicates a condition of mild (type I) IUGR;
  b. a low amount of linoleic acid and arachidonic acid, low depolarization and calcium current and normal inward current indicates a condition of severe (type II) IUGR;
  c. a low amount of linoleic acid and a high amount of arachidonic acid, while all other tests are normal indicates a condition of mild (type I) preeclampsia;
  d. a low amount of arachidonic acid, while all other tests are normal indicates a condition of severe (type II) preeclampsia;
  e. all tests give low results indicates a condition of combined IUGR and preeclampsia; and
  f. all tests are normal indicates the pregnancy is normal.

* * * * *

UNITED STATES PATENT AND TRADEMARK OFFICE
CERTIFICATE OF CORRECTION

| | | |
|---|---|---|
| PATENT NO. | : 7,488,585 B2 | |
| APPLICATION NO. | : 10/525776 | |
| DATED | : February 10, 2009 | |
| INVENTOR(S) | : Hamutal Meiri | |

It is certified that error appears in the above-identified patent and that said Letters Patent is hereby corrected as shown below:

On the title page add in the following:

Related U.S. Application Data:

(60)  Provisional application No. 60/406,687, filed on Aug. 29, 2002.

Signed and Sealed this

Fourteenth Day of April, 2009

JOHN DOLL
*Acting Director of the United States Patent and Trademark Office*